United States Patent [19]

Braid

[11] 4,151,100

[45] Apr. 24, 1979

[54] NOVEL COBALT THIOBIS(ALKYLPHENOLATES) AND ANTIOXIDANT COMPOSITIONS THEREOF

[75] Inventor: Milton Braid, Westmont, N.J.

[73] Assignee: Mobil Oil Corporation, New York, N.Y.

[21] Appl. No.: 853,353

[22] Filed: Nov. 21, 1977

[51] Int. Cl.$^2$ .............. C10M 1/54; C10M 3/48; C10M 5/28; C10M 7/52

[52] U.S. Cl. .............. 252/42.7; 260/45.75 M; 260/439 R

[58] Field of Search .............. 260/439 R, 45.75 M; 252/42.7

[56] References Cited

U.S. PATENT DOCUMENTS

| | | | |
|---|---|---|---|
| 2,346,808 | 4/1944 | Winning et al. | 252/439 R X |
| 2,362,289 | 11/1944 | Mikeska | 252/439 R X |
| 2,362,293 | 11/1944 | McNab et al. | 252/439 R X |
| 2,380,299 | 7/1945 | Evans | 260/45.75 M |
| 2,409,687 | 10/1946 | Rogers et al. | 260/439 R X |
| 3,215,717 | 11/1965 | Foster | 260/439 R |
| 3,390,160 | 6/1968 | Heller et al. | 260/439 R X |
| 3,632,825 | 1/1972 | Jordan | 260/439 R |

*Primary Examiner*—Helen M. S. Sneed
*Attorney, Agent, or Firm*—Charles A. Huggett; Raymond W. Barclay; Howard M. Flournoy

[57] ABSTRACT

Novel cobalt thiobis (alkylphenolates) and coordination compounds thereof with alcohols, alkyl amines, or aryl amines are effective anti-oxidant additives for various organic media such as oils of lubricating viscosity and plastics. Synergistic and improved antioxidant combinations are formed from the admixture of said additives and known antioxidants such as N-phenyl-1-naphthylamine. Additionally, these cobalt thiobis(alkylphenolates), coordination compounds thereof and said combinations are also highly useful as energy quenchers and antisludging agents in organic substrates.

30 Claims, No Drawings

NOVEL COBALT THIOBIS(ALKYLPHENOLATES) AND ANTIOXIDANT COMPOSITIONS THEREOF

BACKGROUND OF THE INVENTION

1. Field of the Invention

This invention relates to cobalt (II) thiobis (alkylphenolates) as novel compounds and to organic compositions, such as lubricants and plastics, normally subject to oxidative degradation, containing a minor amount of said cobalt phenolates, sufficient to impart antioxidant characteristics thereto. This invention further relates to synergistic and improved antioxidant combinations of the cobalt thiobis phenolates in accordance herewith and certain aryl amines and/or hindered phenols. Additionally, this invention relates to organic compositions wherein a minor amount of said novel cobalt (II) thiobis(alkylphenolates) provides effective energy quenching stabilization and antisludging properties.

In a more particular aspect this invention is directed to the above referred to novel cobalt (II) thiobis phenolates and lubricant compositions containing them, which lubricant compositions include oils of lubricating viscosity, hydrocracked lubricating oils, hydraulic oils, mineral oils or fractions thereof, automotive oils, gear oils, transmission fluids, waxes, greases and other forms, natural or synthetic, of lubricants normally requiring the presence of stabilizing agents against oxidative degradation. Contrary to expectations, the subject cobalt (II) thiobis(alkylphenolates) when complexed with certain arylamines, also function well as oxidation inhibitors, i.e. antioxidants, ultraviolet stabilizers and energy quencher stabilizers.

2. Description of the Prior Art

In general, the production of lubricant compositions, for example, lubricating oils produced by hydrocracking, affords a relatively high viscosity index and permits the use of certain stocks that would be unsuitable for other processes. On the other hand, however, hydrocracked lubricating oils tend toward poor stability against ultraviolet light degradation, rapidly forming suspended and/or precipitated insoluble material on exposure to ultraviolet light, such as sunlight, or other sources of actinic radiation. Compounds capable of absorbing ultraviolet light, for example, hydroxybenzophenones, and hydroxyphenyl benzotriazoles, have afforded some improvement in the light stability of hydrocracked oils. Conventional antioxidants have also provided some benefit.

In the literature, Heskins and Guillet in "Mechanism of Ultraviolet Stabilization of Polymers", Macromolecules 1, 97 (1968) first proposed the energy transfer mechanism of ultraviolet protection. Commercially available ultraviolet stabilizers are also listed by class and function and identified as to structure in the Kirk-Othmer Encyclopedia in "Encyclopedia of Chemical Technology", Second Edition, Vol. 21, pp. 115-122. Uri in "Thermal and Photochemical Oxidation of Polymers and Its Prevention", Chemistry and Industry, Mar. 1, 1975, pp. 199-203, cites conventional antioxidant effects (hydroperoxide decomposition and free radical capture) of bis(stilbenedithiolato)nickel and its ultraviolet inhibiting properties. In British Patent specification No. 1,263,910 (1972), there is disclosed bis(stilbenedithiolato)nickel as an antioxidant for plastic materials. The compounds being useful in lube oils and functional fluids. Further, U.S. Pat. Nos. 2,703,786, 2,716,090 and 3,210,277 disclose the use of polyvalent metal (e.g. Ni) salts of alkyl phenol sulfides as oxidation inhibitors and plasticizing agents. Various polyvalent metal (e.g. nickel) compounds are disclosed in the patent literature, for example, U.S. Pat. No. 3,630,897 discloses metal salts (e.g. nickel, iron, zinc) of substituted dithiocarbamic acids and U.S. Pat. No. 3,252,910 discloses compounds such as nickel N,N-substituted dithiooxamides. U.S. Pat. Nos. 2,971,940 and 2,971,941 disclose nickel phenol-phenolate complexes as being useful in stabilizing polyethylene and polypropylene.

None of the foregoing disclosures, however, show organic, e.g., lubricant compositions containing the organo sulfur-containing cobalt (II) complexes described in accordance with this invention.

SUMMARY OF THE INVENTION

This application is predicated on the discoveries of (1) certain novel organosulfur-containing cobalt (II) compounds and (2) that organic compositions of improved anti-oxidant characteristics, ultraviolet light and energy quenching stabilization and antisludging properties are provided when these novel organosulfur cobalt (II) compounds or mixtures of such compounds with arylamines and/or hindered phenols are added thereto in minor effective amounts.

The organic sulfur-containing cobalt (II) compounds in accordance with the present invention include cobalt (II) thiobis(alkylphenolates) having the following structure:

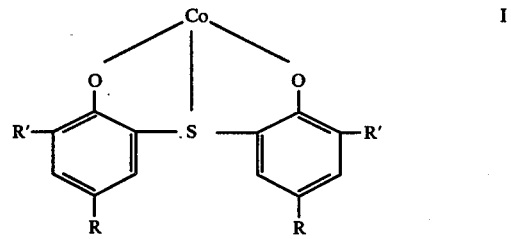

in which R is either hydrogen or an alkyl group having from 1 to about 30 carbon atoms or preferably 1-16 or 4-8 carbon atoms in any isomeric arrangement and R' may be the same as R except that isomers in which the carbon atom attached to the ring is connected to more than two carbon atoms are excluded. Representative of the cobalt (II) thiobis(alkyl-phenolate) complexes are cobalt [2,2'-thiobis-(4-t-octylphenolates)] having the structure:

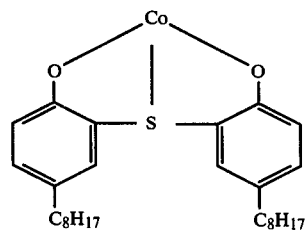

in which $C_8H_{17}$ is 1,1,3,3-tetramethylbutyl and cobalt (II) 2,2'-thiobisphenolate having the structure:

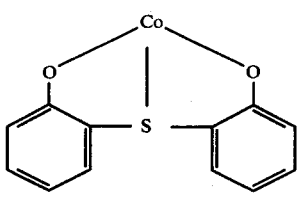

This application therefore is directed to compounds of cobalt (II) prepared by the reaction of cobalt (II) with thiobis(alkylphenol) under appropriate conditions of temperature, pressure and time wherein the product is formed in a 1:1 ratio of cobalt (II) and thiobis(alkylphenolate), e.g. 2,2'-thiobis (4-t-octylphenol).

Also included within the scope of this invention are complexes of the cobalt (II) thiobisphenolates with alkyl- or arylamines. Representative of such complexes is [2,2'-thiobis-(4-t-octylphenolato)]-n-butylamine cobalt (II) having the structure:

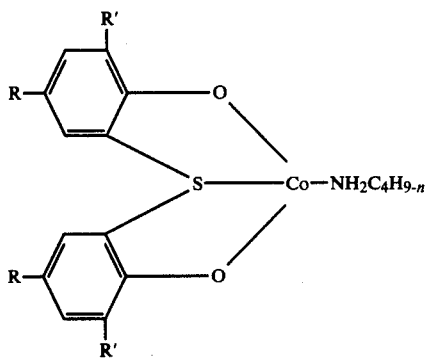

II

Also included are diamine complexes with two molecules of amine. Representative of such compounds is:

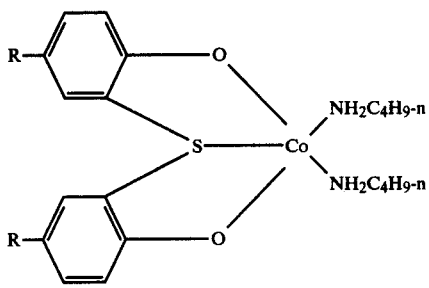

IIa where R and R' are as described above.

Further, the cobalt (II) thiobisphenolate can be made to form a complex with a hydroxylated ligand such as methanol, ethanol, propanol, 2-propanol and the like. A representative compound is [2,2'-thiobis-(4-t-octyl phenolato)]-2-propanol having the structure:

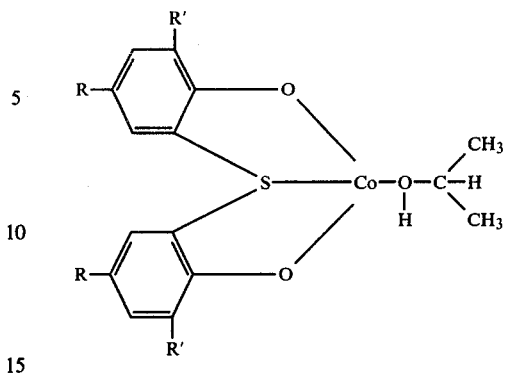

III where R and R' are as described above.

These so-called coordination compounds are also highly advantageous as oxidation inhibitors.

The organosulfur-containing cobalt (II) thiobisphenolates in accordance with this invention can be effectively employed in any amount which is sufficient for imparting to the organic medium, e.g., lubricant, the desired degree of protection against oxidative degradation. In many instances, the cobalt (II) complex is effectively employed in an amount from about 0.01 to about 5%, by weight, and preferably in an amount from about 0.1 to about 2%, by weight, of the organic composition.

The term "cobalt complex," as used herein is intended to include cobalt compounds having a chelate ring formation. As hereinbefore indicated, the organic sulfur-containing cobalt complexes may be incorporated in various organic media which can include oils of lubricating viscosity and also greases in which any of the aforementioned oils are employed as vehicles. In general, synthetic oils can also be effectively protected against oxidative and UV degradation or may also be employed in combination with mineral oils, or as grease vehicles. Typical synthetic vehicles include polyisobutylene, polybutenes, hydrogenated polydecenes, polypropylene glycol, polyethylene glycol, trimethylolpropane esters, neopentyl and pentaerythritol esters, di-(2-ethylhexyl) sebacate, di-(2-ethylhexyl)adipate, dibutyl phthalate, fluorocarbons, silicate esters, silanes, esters of phosphorus-containing acids, liquid ureas, ferrocene derivatives, hydrogenated mineral oils, chain-type polyphenols, siloxanes and silicones (polysiloxanes), alkyl-substituted diphenyl ethers typified by a butyl-substituted bis-(p-phenoxy phenyl) ether, phenoxy-phenylether, etc.

The thiobis(alkylphenols) are readily obtained from a variety of commercial sources.

The cobalt II complexes of the thiobis(alkylphenols) can be prepared in several ways. Reaction of the thiobis(alkylphenol) with a cobalt (II) carboxylate for example cobalt (II) acetate in 1:1 molar ratio may be carried out in a non-reactive solvent such as xylene and the acetic acid may be removed as a binary azeotrope with xylene. The reaction temperature depends on the solvent used and is generally higher than the boiling point of the carboxylic acid liberated. Alternatively, a cobalt II salt such as cobalt II chloride or cobalt II nitrate may be reacted with di-alkali metal salt of a thiobis(alkylphenolate) for example di-potassium or di-sodium thiobis(alkylphenolate) in ethanol or propanol. The insoluble inorganic alkali metal salt formed is separated and the alcohol is then completely removed.

General reaction conditions: as noted previously temperature is dependent upon the solvent used and is usually about 5°–25° C. below the solvent's BP; atmospheric pressure or higher if desired may be used; reaction duration will of course vary with temperature and pressure.

As mentioned hereinabove the novel cobalt thiobis(phenolates) of this invention function as effective antioxidant additives, or provide effective stabilization against ultraviolet degradation and also act as effective energy quencher stabilizers when incorporated into certain organic media. Therefore, this application is further particularly directed to compositions comprising a major amount of an organic medium normally susceptible to oxidative degradation and a minor amount effective to impart antioxidant characteristics thereto and/or to stabilize said composition against ultraviolet degradation and/or to impart energy quenching stabilization and/or antisludging properties thereto of an organosulfur containing cobalt (II) thiobis phenolate and coordination compounds thereof with alkylamines, arylamines, or alcohols.

The additive compounds disclosed herein form synergistic and improved mixtures when used in combination with arylamines and/or hindered phenols. Accordingly, this application is also directed to additive mixtures adapted to impart antioxidative characteristics to an organic medium normally susceptible to oxidative degradation consisting essentially of a cobalt (II) compound selected from the compounds described herein before as structures I, II, IIa and III and an arylamine and/or a hindered phenol.

The arylamines used herein are preferably selected from the group consisting of the following: N-phenyl-1-naphthylamine; N-(4'-t-octylphenyl)-1-naphthylamine; 1,1'-thiobis(N-phenyl-2-naphthylamine); diphenylamine; phenothiazine. Especially preferred are phenyl naphthylamines such as N-phenyl-1-napthylamine, N-(4-t-octylphenyl)-1-naphthylamine and N-phenyl-2-naphthylamine. However, it is understood that this is a non-limiting list and any arylamine appropriate in view of those disclosed above may be used. For purposes of this application it is understood that the term arylamines is meant to include arylaminoquinones, arylaminohydroquinones and phenothiazines.

Any suitable hindered phenolic compound may be used herein. Preferred are those selected from the following non-exhaustive list: 2,6-di-t-butyl-p-cresol; 4,4'-methylenebis-(2-6-di-t-butyl-m-cresol); 4,4'-butylidenebis(6-t-butyl-m-cresol) 4,4'-methylenebis-(2,6-di-t-butylphenol); 2,6-di-t-butylphenol, and 4,4'butylidinebis-(2,6-di-t-butylphenol) 2,4,6-tri-t-butylphenol. Especially preferred is 4,4'-methylenebis-(2,6di-t-butylphenol).

Generally the weight ratio of the cobalt (II) compounds to arylamine and/or hindered phenol is from about 0.01–5.0 to 1.

DESCRIPTION OF SPECIFIC EMBODIMENTS

Examples 1 describes the base lubricant, 3 and 6 describe representative nickel containing organosulfur compounds of the prior art.

Example 2 is a known antioxidant, phenyl-alpha-naphthylamine.

Examples 4, 5 and 7 are cobalt (II) compounds (complexes) in accordance with this invention.

Examples 8, 9 and 10 are synergistic and improved mixtures in accordance with the invention.

EXAMPLE 3

One hundred and fifty grams of the phenol-phenolate described in U.S. Pat. No. 2,971,941 (melting range 147°–149° C.) were added to about 1500 ml of 2-propanol and the mixture was heated and stirred. As the temperature, about 80°–85° C., approached reflux the phenol-phenolate virtually all dissolved. After about 0.25 to 0.5 hr., precipitation of solids began and the mixture became progressively more turbid. The hot mixture was filtered and the solids collected and air dried and then heated under a stream of nitrogen gas at 180°–185° C. for 2.5 hr. Obtained were 65.3 g of nickel 2,2'-thiobis-(4-t-octylphenolate) as a tan colored solid melting above 300° C.

EXAMPLE 4

A sample of cobalt (II) 2,2'thiobis-(4-t-octylphenolate) was prepared as follows:

A mixture of 2,2'-thiobis(4-t-octylphenol) (44.2 g.) and anhydrous potassium carbonate (6.9 g.) was heated in refluxing 2-propanol for about 0.5 hr. and then cobalt (II) acetate tetrahydrate (12.5 g.) was added. The reaction mixture was stirred at reflux temperature for about 4 hr. during which a precipitate of pink solids was formed. The mixture was filtered and the solids were washed with water and dried. The solids were recystallized from 2-propanol and the resulting pink solid, m.p. 355°–357° C. was dealcoholated by heating at 140° C. at less than 0.1 mm of mercury to give the cobalt 2,2'-thiobis-(4-t-octylphenolate) as a brownish solid m.p. greater than 360° C.

EXAMPLE 5

A sample of [2,2'-thiobis-(4-t-octylphenolato)]-2-propanol cobalt (II) was prepared in the following manner:

2,2'-thiobis-(4-t-octylphenol) (88.4 g.) and cobalt (II) acetate tetrahydrate (49.8 g.) were heated in xylene until removal of water was complete and the xylene distillate was free of detectable acetic acid. The reaction mixture was cooled and filtered. Xylene solvent was distilled from the filtrate and the residue was treated with reluxing 2-propanol. The resulting complex, [2,2'-thiobis-(4-t-octylphenolato)]-2-propanol cobalt II, was collected on a filter as a salmon pink solid, m.p. 245°–267° C. (capillary); greater than 300° C. (open stage).

Anal. Calc'd for $C_{31}H_{48}O_3SCo$:C, 66.52; H, 8.64; S, 5.73; Co, 10.53. Found: C, 67.22, H, 8.71; S, 5.41; Co, 10.52.

EXAMPLE 6

[2,2'-thiobis-4-t-octyphenolato)]-n-butylamine nickel (II) was prepared in accordance with the procedure set forth in Example 8 of U.S. Pat. No. 3,215,717.

EXAMPLE 7a

[2,2'-thiobis-(4-t-octylphenolato)-di-n-butylamine cobalt (II) was prepared by heating [2,2'-thiobis-(4-t-octylphenolato)]-2-propanol cobalt II (Example 5) with an excess of n-butylamine. Thus, 1 g. of the 2-propanol complex was dissolved in 20 ml. of n-butylamine and refluxed for 0.25 hr. and the excess amine and displaced alcohol were removed by distillation. Traces of adsorbed amine were removed by heating the residue at 110° C. at a reduced pressure of 13 mm. of mercury. The complex, [2,2'-thiobis-(4-t-octylphenolato)]-di-n- butylamine cobalt II, was a dark brown solid, m.p. 276°–280° C. (open stage), 115°–118° C. (Capillary).

Anal. Calc'd for $C_{36}H_{62}O_2N_2SCo$: C, 66.95; H, 9.68; S, 4.96; N, 4.34, Co, 9.12. Found: C, 66.61; H, 9.51; S, 4.54; N, 4.02; Co, 9.05.

EXAMPLE 7b

To [2,2'-thiobis-(4-t-octylphenolato)]-2-propanol cobalt II (11.2 g.) in 100 ml. of cyclohexane there added a solution of n-butylamine (1.5 g.) in 50 ml. of cyclohexane and the mixture was heated at reflux for about 3 hr. Solvent and displaced 2-propanol were removed by distillation. The residue was crystallized from 2-propanol. [2,2'-thiobis-(4-t-octylphenolato)]-n-butylamine cobalt II was obtained as a brown solid, m.p. 280°–285° C. (open stage).

Anal. Calc'd for $C_{32}H_{51}O_2NSCo$: N, 2.45; S, 5.60; Co, 10.29; Found: N, 2.12; S, 5.21; Co. 10.50.

In order to evaluate the effectiveness of the organosulfur-containing cobalt (II) phenolates of the present invention in lubricant media the following tests were employed:

OXYGEN ABSORPTION TEST

Oxidations were conducted in an oxygen circulation apparatus of the type described by Dornte, R. W. Dornte, *Ind. Engr. Chem.*, 28, 26 (1936), modified so the rate of oxygen adsorption could be recorded automatically. The 30 g. sample was placed in a 28×260 mm tube and allowed to equilibrate thermally before the oxygen flow was begun. Oxygen was introduced to the sample at a rate of 5 l/hr. through a fritted glass disk 3 mm from the bottom of the tube. The inhibition period, $t_{1.0}$, was taken as the time required for the absorption of 1.0 mol oxygen per kg of sample.

The data from this test are recorded below in Table 1. These data as do the data in Table 2 include nickel compounds (Examples 3 and 6) to illustrate the unexpected and surprising superiority of cobalt compounds in accordance with this invention over such prior art compounds.

Table 1 demonstrates the highly effective antioxidant properties of cobalt (II) phenolates, coordination compounds thereof and additive mixtures of this invention in mineral-oil base stock.

The organo-cobalt (II) complexes of this invention were also tested in a *Catalytic Oxidation Test* for lubricants, using as the base medium a synthetic ester lubricant. This lubricant is prepared by the esterification of technical grade pentaerythritol with a mixture of commercial monocarboxylic acids - valeric and pelargonic acids. The test lubricant composition is subjected to a stream of air which is bubbled through the composition at a rate of 5 liters per hour at 450° F. for 24 hours. Present in the composition are metals commonly used as materials of engine construction, namely:

(a) 15.6 sq. in. of sand-blasted iron wire,
(b) 0.78 sq. in. of polished copper wire,
(c) 0.87 sq. in. of polished aluminum wire, and
(d) 0.167 sq. in. of polished lead surface.

Inhibitors for oil are rated on the basis of prevention of oil deterioration as measured by the increase in acid formation or neutralization number ($\Delta NN$) and kinematic viscosity ($\Delta KV$) occasioned by the oxidation. The results of the test are reported in Tables 2 and 3.

As will be noted from Table 2, the oxidation life of the ester base oil was markedly increased by the antioxidant effect imparted by the cobalt II additives in accordance with the present invention.

TABLE 2

| | Catalytic Oxidation Tests of Ester Base Stock Containing 2.0 wt. % Additives | | |
|---|---|---|---|
| Ex. | Additive | Neutralization Number Increase | Increase in kinematic Viscosity at 100° F.% |
| 1 | None | 8.3 | 586 |
| 2 | | 3.6 | 82 |
| 3 | Nickel 2,2'-thiobis(4-t-octylphenolate) | 4 | 83 |
| 5 | [2,2'-thiobis-(4-t-octyl phenolato)]-2-propanol cobalt (II) | 1.8 | 57 |

TABLE I

| | Inhibition of Hexadecane Autoxidation at 175° C.[1] | | | |
|---|---|---|---|---|
| Example | Additives | Conc. of Ni or Co(II) complex, mol/Kg. | Conc. of Coadditive, mol/Kg. | Inhibition Period for Oxygen Absorption Hr. ($t_{1.0}$)[2] |
| 1 | None | — | — | 1.2/1.1 |
| 2 | N-Phenyl-1-naphthylamine | 0.005 | — | 6.3/5.8 |
| 3 | Nickel 2,2'-thiobis (4-t-octyl phenolate) | 0.005 | — | 3.7/5.3 |
| 4 | Cobalt(II)2,2'-thiobis-(4-t-octyl phenolate) | 0.005 | — | 10.1 |
| 5 | [2,2'-Thiobis-(4-t-octylphenolato)]-2-propanol Cobalt II | 0.005 | — | 11/13.5 |
| 6 | [2,2'-Thiobis-(4-t-octylphenolato)]-n-butylamine Nickel II | 0.005 | — | 7.1/7.8 |
| 7a | [2,2'-Thiobis-(4-t-octylphenolato)]-di-n-butylamine Cobalt II | 0.005 | — | 15.2 |
| 8 | Example 4 + Coadditive Example 2 | 0.0025 | 0.0025 | 28.3 |
| 9 | Example 5 + Coadditive Example 2 | 0.0025 | 0.0025 | 43.5 |
| 10 | Example 7 + Coadditive Example 2 | 0.0025 | 0.0025 | 48.1 |

[1]Modified Dornte Test.
[2]Time (hr.) required to absorb 1 mol. of oxygen/Kg. of oil.

TABLE 2-continued

Catalytic Oxidation Tests of Ester Base Stock Containing 2.0 wt. % Additives

| Ex. | Additive | Neutralization Number Increase | Increase in kinematic Viscosity at 100° F.% |
|---|---|---|---|
| 6 | [2,2'-thiobis-(4-t-octylphenolato)]-n-butylamine nickel II | 6.6 | 107 |
| 7b | [2,2'-thiobis-(4-t-octylphenolato)]n-butylamine Cobalt II | 3.4 | 45 |
| 8 | Phenothiazine | 3 | 63 |
| 9 | 4',4'-methylenebis-(2-t-di-t-butylphenol) | 2.8 | 55 |

TABLE 3

Catalytic Oxidation Tests of Ester Base Stock

| | Conc. wt.% | Conc. Additive wt.% | Neutralization Number Increase | Increase in Kinematic Viscosity at 100° F.,% | Sludge |
|---|---|---|---|---|---|
| Ex. 5 & Coadditive Ex. 2 | 1 | 1 | 0.45 | .28 | nil |
| Ex. 5 & Coadditive 4,4'-methylenebis-(2,6-di-t-butylphenol) | 1 | 1 | 2.8 | 53 | nil |
| Ex. 5 & Coadditive Phenothiazine | 1 | 0.5 | 3.0 | 89 | nil |
| Ex. 5 & Coadditive Diphenylamine | 1 | 1 | 2.3 | 74 | Heavy |
| Ex. 7b + Coadditive Ex. 2 | 1 | 1 | 3.5 | 43 | Light |

While this invention has been described with reference to preferred compositions and components therefor, it will be understood by those skilled in the art that departure from the preferred embodiments can be effectively made and are within the scope of the specification.

What is claimed is:

1. A compound derived from Cobalt II and a thiobis-(alkylphenol) containing a ratio of one cobalt atom to one molecule of the thiobis(alkylphenolate) having the general structure:

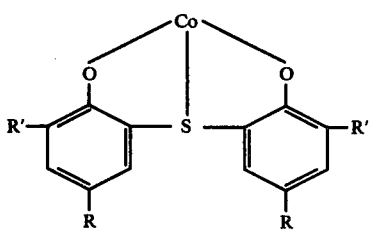

where R and R' are H or an alkyl group having from 1 to about 30 carbon atoms and R' is the same as R except that the carbon atom attached to the ring is connected to no more than 2 carbon atoms.

2. The compound of claim 1 in which R and R' are each alkyl groups having from 1 to about 16 carbon atoms.

3. The compound of claim 2 in which R and R' are each alkyl groups containing from 4 to about 8 carbon atoms.

4. The compound of claim 3 where R and R' are $C_8H_{17}$.

5. The compound of claim 4 where R is (t-octyl).

6. The compound of claim 1 complexed with n-butylamine and having the following structure:

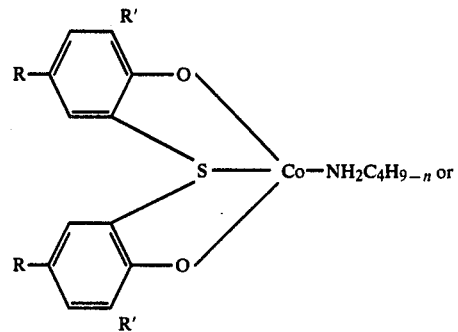

7. The compound of claim 6 where R is $C_8H_{17}$.

8. The compound of claim 7 where R is (t-octyl).

9. The compound of claim 1 complexed with 2-propanol and having the following structure:

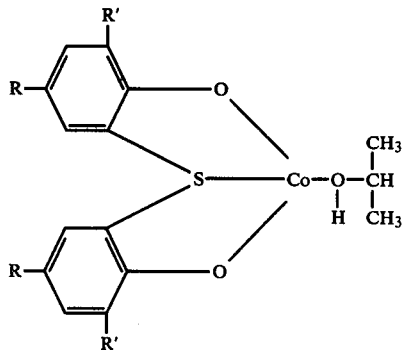

10. The compound of claim 9 where R is $C_8H_{17}$.

11. The compound of claim 10 where R is (t-octyl).

12. The compound of claim 10 where R is 1,1,3,3-tetramethylbutyl, and R' is H.

13. A composition comprising a major proportion of an organic medium normally susceptible to oxidative

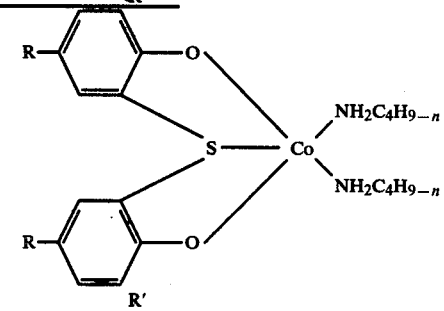

degradation and a minor amount, sufficient to impart antioxidant properties, ultraviolet stabilization and energy quenching stabilization thereto, of a compound as described in claim 1.

14. A composition comprising a major proportion of an organic medium normally susceptible to oxidative degradation and a minor amount sufficient to impart antioxidant properties, ultraviolet stabilization and energy quenching stabilization thereto of a compound as described in claim 6.

15. A composition comprising a major proportion of an organic medium normally susceptible to oxidative degradation and a minor amount sufficient to impart antioxidant properties, ultraviolet stabilization and energy quenching stabilization thereto of a compound as described in claim 9.

16. The composition of claim 13 wherein the organic medium is selected from the group consisting of fuel oils, and lubricant compositions comprising oils of lubricant viscosity or greases prepared therefrom, hydrocracked oils, hydraulic oils, mineral oils or fractions thereof, synthetic oils or mixtures of synthetic or mineral oils, ester base oils or mixtures thereof with mineral oils, automotive oils, gear oils, transmission fluids, or waxes.

17. The composition of claim 16 wherein the organic medium is an oil of lubricant viscosity.

18. The composition of claim 17 wherein the oil of lubricant viscosity is a mineral oil.

19. The composition of claim 17 wherein the oil of lubricant viscosity is a synthetic oil.

20. The composition of claim 16 wherein the oil of lubricant viscosity is an ester-base oil.

21. The composition of claim 16 wherein said composition is a grease.

22. The composition of claim 13 comprising said compound in combination with an aryl amine and/or a hindered phenol.

23. The composition of claim 14 comprising said compound in combination with an aryl amine and/or a hindered phenol.

24. The composition of claim 15 comprising said compound in combination with an aryl amine and/or a hindered phenol.

25. An additive mixture adapted to impart antioxidative characteristics to an organic medium normally susceptible to oxidative degradation consisting essentially of a cobalt (II) compound selected from:

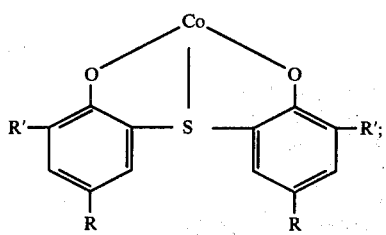

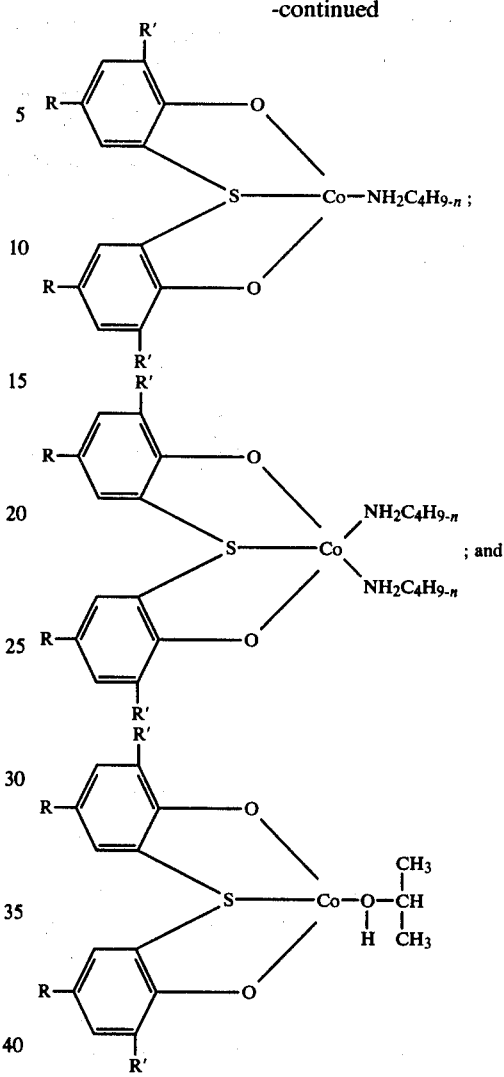

where the R and R' groups thereof are H or alkyl of from 1 to about 30 carbon atoms and an arylamine and hindered phenol in which the weight ratio of cobalt (II) compound to aryl amine and/or hindered phenol is from about 0.01:5.0 to 1.

26. The mixture of claim 25 wherein the arylamine is selected from N-phenyl-1-naphthylamine; N-phenyl-2-naphthylamine; N-(4-t-octylphenyl)-1-naphthylamine; 4,4'-thiobis-(n-phenyl-1-naphthylamine); 1,1'-thiobis-(N-phenyl-2-naphthylamine); 4,4'-di-t-octyldiphenylamine; diphenylamine; triphenylamine; dinaphthylamine and phenothiazine.

27. The mixture of claim 25 wherein the arylamine is N-phenyl-1-naphthylamine.

28. The mixture of claim 25 wherein the hindered phenol is selected from the group consisting of 2,6-di-t-butyl-p-cresol; 4,4'-methylenebis-(2-6-di-t-butyl-m-cresol); 4,4'-butylidinebis (6-t-butyl-m-cresol); 4,4'-methylenebis (2,6-di-t-butylphenol); 2,6-di-t-butylphenol and 4,4'-butylidine-bis(2,6-di-t-butylphenol).

29. The mixture of claim 25 wherein the hindered phenol is 4,4'-methylenebis(2,6-di-t-butylphenol).

30. The mixture of claim 25 wherein the cobalt (II) compound is cobalt (II) 2,2'-thiobis-(4-t-octyl)phenolate; and wherein the arylamine is N-phenyl-1-naphthylamine.

* * * * *